US012280247B2

(12) United States Patent
Yan et al.

(10) Patent No.: US 12,280,247 B2
(45) Date of Patent: Apr. 22, 2025

(54) NEEDLE COVER REMOVING DEVICE AND A METHOD FOR REMOVING THE NEEDLE COVER OF AN INJECTION DEVICE

(71) Applicant: Becton Dickinson France, Le Pont de Claix (FR)

(72) Inventors: Bo Yan, Shanghai (CN); Longxiang Huang, Suzhou (CN)

(73) Assignee: Becton Dickinson France, Le Pont de Claix (FR)

( * ) Notice: Subject to any disclaimer, the term of this patent is extended or adjusted under 35 U.S.C. 154(b) by 827 days.

(21) Appl. No.: 17/436,412

(22) PCT Filed: Mar. 3, 2020

(86) PCT No.: PCT/EP2020/055560
§ 371 (c)(1),
(2) Date: Sep. 3, 2021

(87) PCT Pub. No.: WO2020/178285
PCT Pub. Date: Sep. 10, 2020

(65) Prior Publication Data
US 2022/0134020 A1 May 5, 2022

(30) Foreign Application Priority Data
Mar. 4, 2019 (EP) ..................................... 19305248

(51) Int. Cl.
*A61M 5/32* (2006.01)
(52) U.S. Cl.
CPC ..... *A61M 5/3204* (2013.01); *A61M 2205/106* (2013.01); *A61M 2205/14* (2013.01); *Y10T 29/49822* (2015.01)

(58) Field of Classification Search
CPC .......... A61M 5/3204; A61M 2205/106; A61M 2205/14; A61M 2205/10; Y10T 29/49822
See application file for complete search history.

(56) References Cited

U.S. PATENT DOCUMENTS

| 8,708,970 B2 | 4/2014 | Giambattista et al. |
| 2012/0035542 A1 | 2/2012 | Pongprairochana |

(Continued)

FOREIGN PATENT DOCUMENTS

| CA | 2437514 A1 * | 2/2005 | .......... A61M 5/3202 |
| CN | 102119037 A | 7/2011 | |

(Continued)

OTHER PUBLICATIONS

Arinobe Manabu; WO-2014045336-A1 Machine Translation (Year: 2014).*

*Primary Examiner* — Lee A Holly
(74) *Attorney, Agent, or Firm* — The Webb Law Firm (57) ABSTRACT

The removing device is configured to remove a needle cover removably mounted on a distal tip of an injection device comprising a barrel. The removing device comprises a housing including a holder configured to hold the injection device and a needle cover remover configured to remove the needle cover from the injection device, a first abutment member provided on the holder and being configured to abut against the injection device, a second abutment member provided on the needle cover remover, and being configured to abut against the needle cover, and displacement means configured to displace the needle cover remover relative to the holder in a translational direction so that the first and second abutment members translationally move away from each other in order to separate the needle cover from the injection device.

13 Claims, 6 Drawing Sheets

(56) References Cited

U.S. PATENT DOCUMENTS

2012/0241042 A1  9/2012  Strangis
2018/0147366 A1  5/2018  Aneas

FOREIGN PATENT DOCUMENTS

| JP | 201198133 A | 5/2011 | | |
|---|---|---|---|---|
| WO | WO-2010112090 A1 | * | 10/2010 | .............. A61M 5/20 |
| WO | WO-2014045336 A1 | * | 3/2014 | ............ A61M 5/002 |

* cited by examiner

NEEDLE COVER REMOVING DEVICE AND A METHOD FOR REMOVING THE NEEDLE COVER OF AN INJECTION DEVICE

CROSS-REFERENCE TO RELATED APPLICATIONS

This application is the United States national phase of International Application No. PCT/EP2020/055560 filed Mar. 3, 2020, and claims priority to European Patent Application No. 19305248.7 filed Mar. 4, 2019, the disclosures of which are hereby incorporated by reference in their entirety.

BACKGROUND OF THE INVENTION

Field of the Invention

The present invention relates to a removing device configured to remove a needle cover of an injection device such as a syringe, and a method for removing the needle cover of an injection device.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to an injection device whose needle cover is intended to be removed by the removing device of the invention, and the "proximal direction" is to be understood as meaning the opposite direction to said direction of injection, that is to say the direction towards the user's hand holding the injection device for an injection operation.

Description of Related Art

Injection devices, for example pre-fillable or prefilled syringes, usually comprise a hollow body or barrel forming a container for a medical product. This body comprises a distal end, usually provided with a needle, and a proximal end, provided with a flange. These injection devices are usually furnished with a plunger rod whose distal end comprises a piston which, during the injection phase and under the action of a distal pressure exerted by the user on the piston rod, pushes the product through the injection needle.

In order to maintain sterility prior to use and to reduce the risk of incurring an accidental needle-stick, protection of the needle is important. Injection devices are thus supplied with a needle cover that is mounted on the tip of the barrel so as to enclose the needle.

Before injection, a user typically holds the syringe body in one hand, the needle cover in the second hand, and exerts opposite forces to separate the injection device itself and the needle cover. This uncovers the injection needle and then allows the user to perform the injection.

However, the removal of the needle cover comprises risks of needle stick injury. The sudden separation of the syringe body and of the needle cover may cause a spring back movement of one or both user's hands. Consequently, the uncovered needle may stick into the user's hand that holds the removed needle cover.

Besides, the separation force required to pull the needle cover off the syringe body needs to exceed the friction forces between the syringe body and the needle cover. This separation force may sometimes be quite high so that risks of a spring back movement causing a needle stick injury increase. A professional user, such as a nurse, usually has to perform multiple injections a day. The repeated removals of the needle covers may cause tiredness and therefore increase risks of needle stick injury.

Furthermore, the separation movement of the user's hands pulling in opposite direction does not always follow a straight path. There is thus a risk that the needle bends during removal of the needle cover. A bent needle might however be unusable or cause pain when inserted into an injection site.

It is known from document CA2437514 a device for removing syringe needle cap. The document US2012241042 further discloses an automated syringe filler and loading apparatus. Document WO2014045336 discloses a syringe packaging container. It is further known from document US2012035542 an injection device equipped with a compartment articulated to receive a syringe.

SUMMARY OF THE INVENTION

In this context, an aspect of the invention is to provide a device that allows safe repeated removals of the needle cover of an injection device without risk of needle stick injury for a user and without risk to bend the needle.

An aspect of the invention is a removing device configured to remove a needle cover removably mounted on the distal tip of an injection device comprising a barrel, the removing device comprising:
 a housing including a holder configured to hold the injection device and a needle cover remover configured to remove the needle cover from the injection device,
 a first abutment member provided on the holder, and being configured to abut against said injection device,
 a second abutment member provided on the needle cover remover, and being configured to abut against the needle cover,
 displacement means configured to displace the needle cover remover relative to the holder in a translational direction so that the first and second abutment members translationally move away from each other in order to separate the needle cover from the injection device.

Preferably, the displacement means are configured to displace the needle cover remover relative to the holder in a translational direction so that the second abutment member translationally moves away from the first abutment in order to separate the needle cover from the injection device.

Preferably, the first abutment member provided on the holder is configured to abut against the barrel of the injection device, more preferably against a distal face of the barrel of the injection device, such as a distal shoulder of the barrel, or to abut against a distal face of a flange of the barrel. Preferably, the second abutment member provided on the needle cover remover is configured to abut against a proximal face, such as the proximal end, of the needle cover. Preferably, the second abutment member provided on the needle cover remover extends parallel to the first abutment member provided on the holder.

Advantageously, the holder is fixed relative to the housing and the needle cover remover is movable relative to the holder and the housing. This allows removal of the needle cover, so that a user does not have to touch the needle cover. As a result, the safety is improved. Typically, the injection device comprises a barrel defining a flange and a distal tip which may be provided with a needle, and a plunger rod actuating a piston arranged inside the barrel. Said barrel may comprise a distal shoulder. The needle may be covered by a needle cover. A groove may be comprised between the shoulder of the injection device and the proximal part of the needle cover.

The removing device of the invention thus allows a safe removal of the needle cover from the injection device, without risk of hurt or pain for the user. The removing of the needle cover from the injection device is no more carried out by the user's hands, but instead by the second abutment member of the needle cover remover, so that there is no risk of spring back movement, and no risk of needle stick injury. The user indeed never has to grasp, even touch, the needle cover during the removal of the needle cover. Besides, the translation movement of the needle cover remover, and thus of the needle cover, avoids bending the needle during the removal of the needle cover.

In embodiments, one or both of the first and second abutment members are configured to insert into a groove delimited between the barrel and the needle cover.

In embodiments, at least one of the first and second abutment members is plate-shaped, preferably both of the first and second abutment members are plate-shaped.

In embodiments, at least one of the first and second abutment members has a notch configured to receive a portion of the injection device, preferably both of the first and second abutment members have a notch. Said notch may be U-shaped.

This allows a fast and easy positioning of the injection device, so as to increase the number of needle cover removals per time unit. The portion received by the notch may be the distal tip of the injection device, the flange of the injection device, or the proximal face of the needle cover.

In embodiments, the holder comprises a longitudinal recess configured to support the barrel of the injection device, said longitudinal recess having a proximal end and a distal end opposite the proximal end, the first abutment member extending either at the proximal or at the distal end of said longitudinal recess.

In embodiments, the housing comprises a retaining element configured to block a proximal movement of a flange of the injection device.

This improves safety, since the injection is prevented to move along the longitudinal recess.

In embodiments, the needle cover remover comprises at least one protective wall configured to extend on at least one side of the needle cover, preferably the needle cover remover comprises two protective walls configured to extend on both sides of the needle cover.

The at least one protective wall may guide ejection of the needle cover during the removal of this needle cover and extend on at least one side of the needle after removal of the needle cover, once the needle cover remover returns to the initial position. This further limit risks of needle stick injury.

In embodiments, the removing device comprises a collector configured to collect the removed needle cover. Therefore, the user does not have to touch the needle cover, thus improving safety of the user.

In embodiments, the removing device comprises guiding means configured to guide the removed needle cover to the collector.

Advantageously, the collector comprises a well and an access opening leading into this well, the well being configured to receive the removed needle cover. In embodiments, the displacement means comprise an actuator, which may be mechanical or electric.

When the actuator is mechanical, the displacement means may comprise a handle graspable by a user and rotatably mounted onto the housing between a rest position and an activation position, and a connecting rod coupling the handle to the second abutment member so that rotation of the handle from the rest position to the activation position causes the second abutment member and the first abutment member to move away from each other in order to pull off the needle cover.

Preferably, in this embodiment, the rotation of the handle from the rest position to the activation position causes the second abutment member to move away from the first abutment member in order to pull off the needle cover.

Advantageously, in this embodiment, the first abutment member is configured to abut against the flange of the barrel, more specifically against a distal face of said flange.

When the actuator is electric, the removal of the needle cover is automated and repeated removals do not tire the user. When the actuator is electric, the removing device may comprise a sensor configured to detect that an injection device is supported by the holder.

This increases safety and efficiency of the removing device.

Advantageously, in this embodiment the first abutment member is configured to abut against a distal shoulder of the barrel of said injection device, the first and second abutment members contacting each other in an initial position of the needle cover remover relative to the holder.

In embodiments, the housing comprises a preparatory support configured to support another injection device next to the holder. Therefore, a user may pre-position an injection device while another injection device is put on the holder for removing the needle cover. Thanks to this preparatory support, the number of needle cover removals per time unit may be increased.

Another aspect of the invention is a method for removing the needle cover of an injection device, said method comprising the steps of:
  positioning the injection device on the holder of the removing device as above-described, so that the first abutment member abuts against the injection device, preferably against the barrel or the flange of said injection device, more preferably against a distal face of the barrel or of the flange of said injection device, and the second abutment member abuts against the needle cover, preferably against a proximal face of the needle cover, and
  activating the displacement means so that the first and second abutment members move away from each other, thereby pulling the needle cover off the injection device.

Preferably, during the step of activating the displacement means of the method of the invention, the second abutment member translationally moves away from the first abutment member.

BRIEF DESCRIPTION OF THE DRAWINGS

The invention and the advantages arising therefrom will clearly emerge from the detailed description that is given below with reference to the appended drawings as follows.

DETAILED DESCRIPTION

Figure 1:
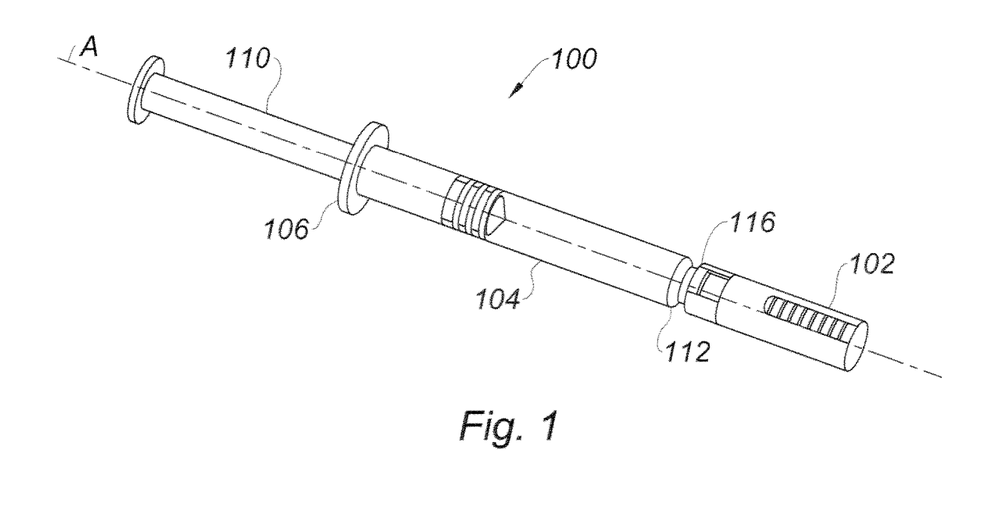
FIG. 1 represents an injection device and a needle cover.
Figure 5:
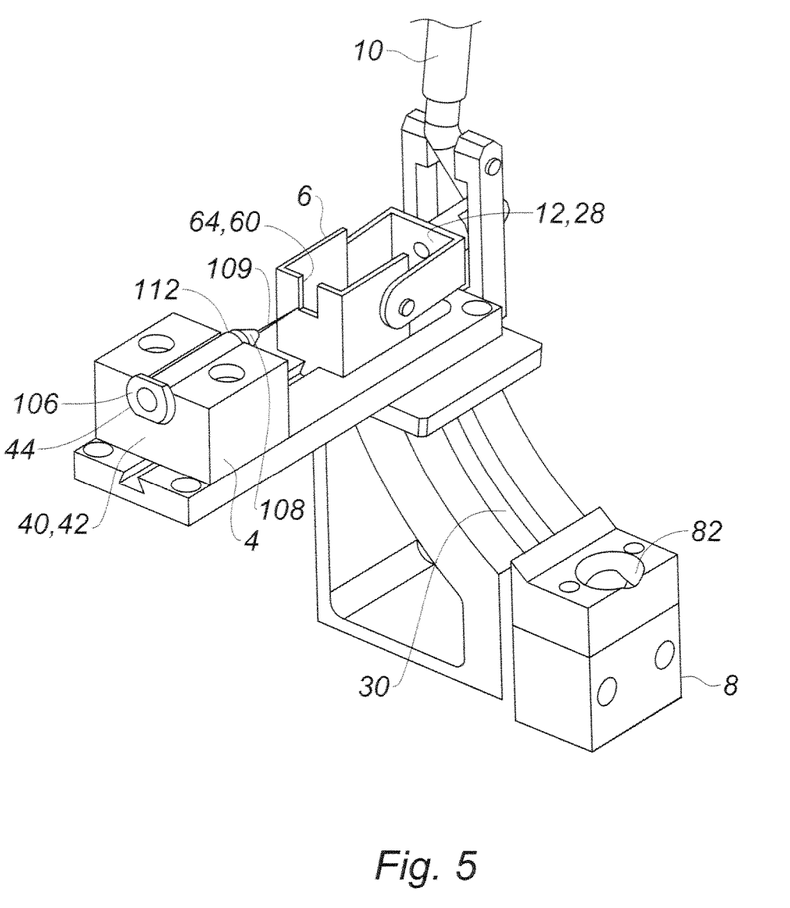
FIG. 5 is a partial perspective view of a removing device according to an embodiment of the invention.

With reference to FIG. 1 is shown an injection device 100. Said injection device 100 may comprise a barrel 104 extending along a longitudinal axis A, a flange 106, a distal tip 108 provided with a needle 109 as shown on FIG. 5, and a plunger rod 110 actuating a piston arranged insided the barrel 104. The barrel 104 of the injection device may comprise a distal shoulder 112. Said distal shoulder 112 may be provided at a distal end of the barrel 104. The distal tip 108 of the injection device 100 may distally protrude from the distal shoulder 112. A needle cover 102 may be sealingly and removably mounted on the distal tip of the injection device. The injection device 100 may be a pre-fillable or a prefilled syringe.

Figure 2:
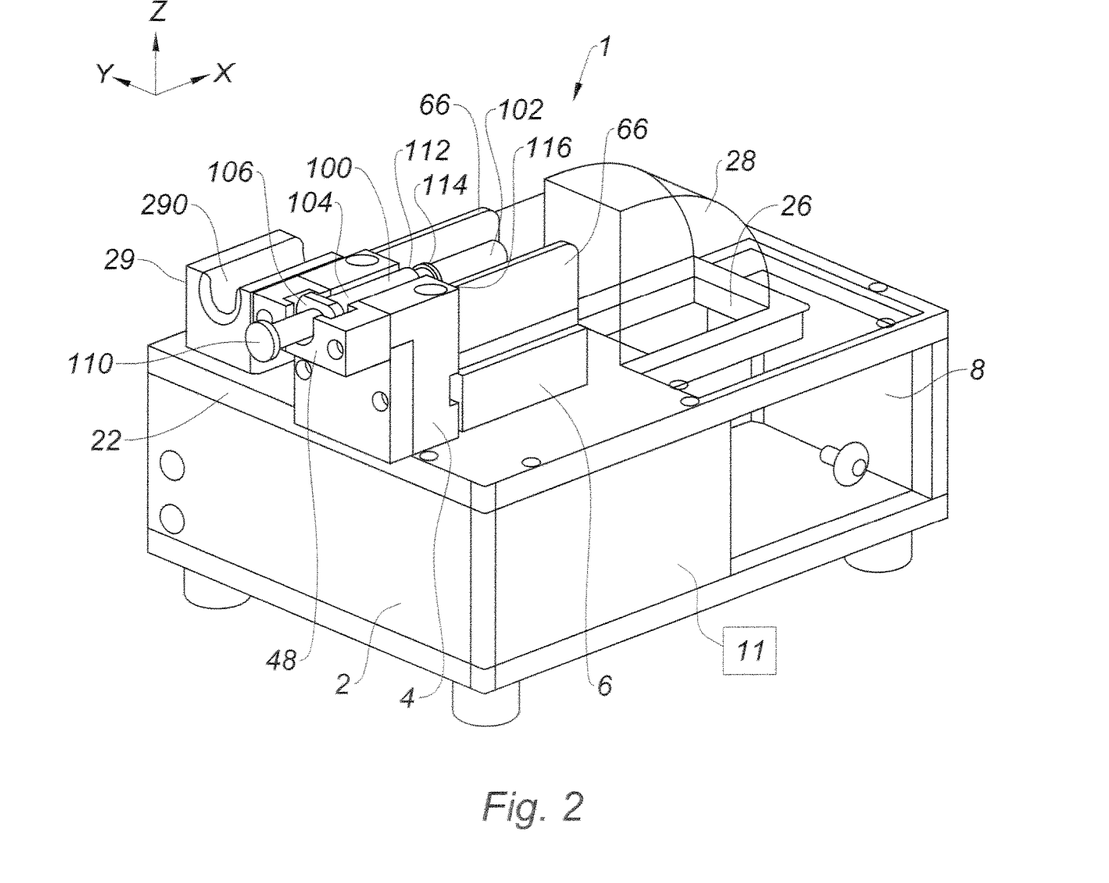
FIG. 2 is a perspective view of a removing device according to an embodiment of the invention.

With reference to FIG. 2, a removing device 1 according to an embodiment of the invention is represented. The removing device 1 is configured to remove a needle cover 102 from an injection device 100.

Figure 4:
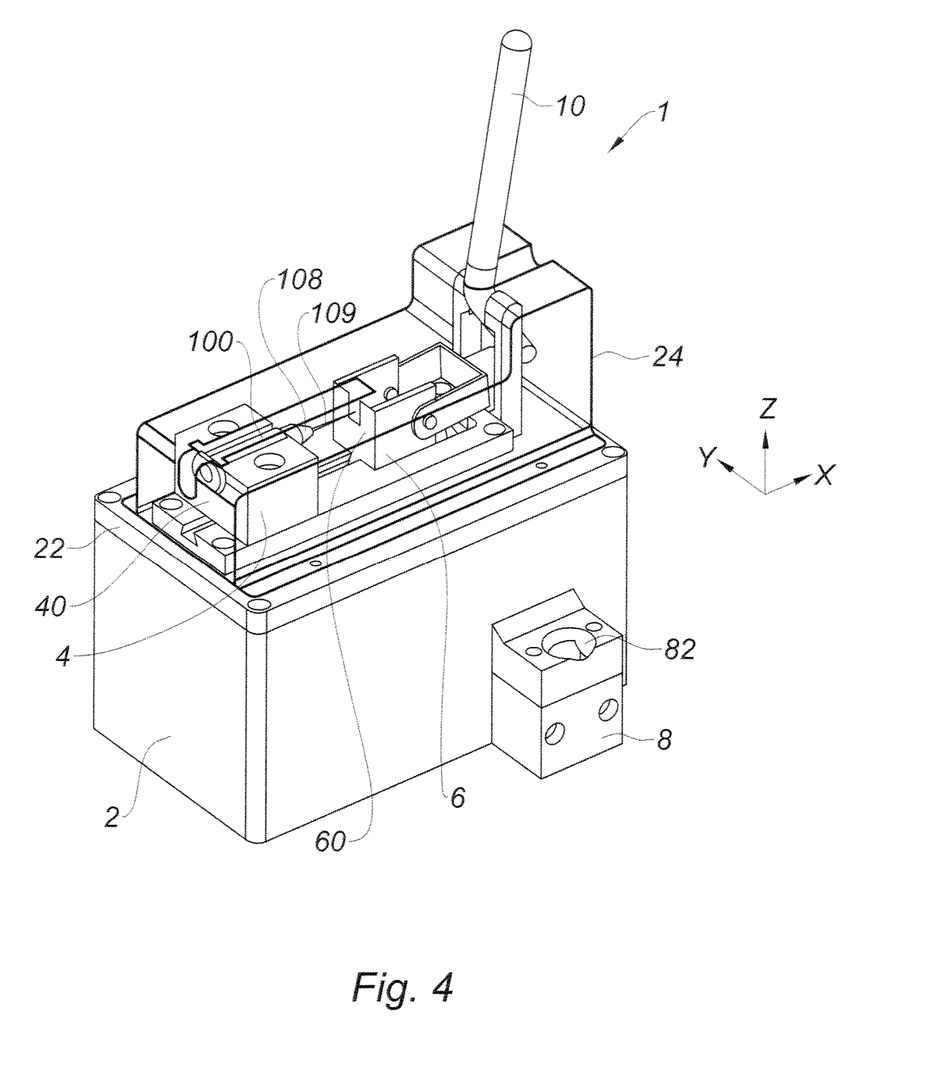
FIG. 4 is a perspective view of a removing device according to an embodiment of the invention.

With reference to FIG. 2 or 4, the removing device 1 comprises a housing 2. The housing 2 supports a holder 4 and a needle cover remover 6. As shown on FIG. 2 or 4, the holder 4 supports the injection device 100, and the needle cover remover 6 is configured to remove the needle cover 102 from the injection device 100. When the injection device 100 is supported by the holder 4, the axis A of the injection device is parallel to the axis X.

Figure 3:
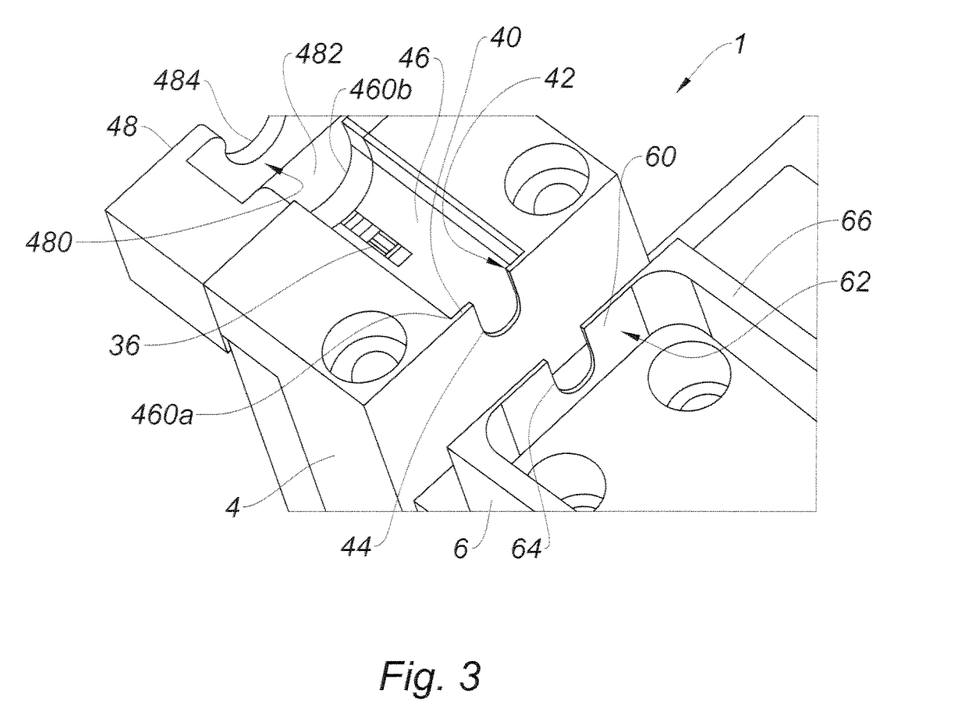
FIG. 3 is a perspective view of the holder of a removing device according to an embodiment of the invention.

As better shown on FIG. 3, the holder 4 comprises a first abutment member 40 that is configured to abut against a distal face of the injection device 100, whereas the needle cover remover 6 comprises a second abutment member 60 that is configured to abut against a proximal face of the needle cover 102. By distal, resectively proximal, face is meant a distally, respectively proximally oriented face with regard to the longitudinal direction X of the injection device.

The removing device 1 further comprises displacement means configured to move the first and second abutment members 40, 60 away from each other in the translational direction X, so as to pull the needle cover 102 off the injection device 100.

As illustrated on the figures, the first abutment member 40 and the second abutment member 60 are movable relative to each other between an initial position (FIG. 2), wherein the first and the second abutment members 40, 60 may be close from each other so that the holder 4 and the needle cover 102 may receive an injection device 100 equipped with a needle cover 102, and an ejection position (FIGS. 3, 4, 5, 7), wherein the first and the second abutment members 40, 60 may be distant and further from each other than in the initial position so that the needle cover 102 may be pulled off the injection device 100.

The first and the second abutment members 40, 60 may contact each other in the initial position. The initial position may thus be a back to back position of the first and the second abutment members 40, 60.

The distance from the initial position to the ejection position is preferably equal to or greater than half of the length of the distal tip 108 of the injection device 100, preferably equal to or greater than the length of the distal tip 108 of the injection device 100.

In a preferred embodiment, the holder 4, and thus the first abutment member 40 is fixed relative to the housing 2 while the second abutment member 60, and thus the needle cover remover 6 is movable relative to the housing 2 and to said first abutment member 40. It should be noted that the first and second abutment members 40, 60 may respectively be fixed relative to the holder 4 and the needle cover remover 6, so that the movement of the first and second abutment members 40, 60 is due to the movement of the holder 4 and the needle cover remover 6 relative to each other.

As shown on FIGS. 2 and 4, the housing 2 may be a box-shaped housing 2. This box-shaped housing 2 may comprise a top plate 22 supporting the holder 4 and the needle cover remover 6, whereas the displacement means (not shown) may be arranged inside the box-shaped housing 2, i.e. beneath the top plate 22.

As shown on FIG. 4, the housing 2 may comprise an enclosure 24 enclosing the holder 4 and the needle cover remover 6, and possibly the displacement means. The enclosure 24 has a window extending in the longitudinal direction X above the holder 4 and the needle cover remover 6 in the initial position so that a user may put the injection device 100 down onto the holder 4 and the needle cover remover 6, and then remove the injection device 100 once the needle is uncovered. The enclosure 24 may also comprise an aperture allowing a user to activate the displacement means. The enclosure 24 may be fixed onto the top plate 22.

As represented on FIG. 3, the first abutment member 40 defines a proximal abutment surface 42 that is configured to abut against a distal face of either the flange 106 (see FIGS. 4, 5, 7) or a distal shoulder 112 of the barrel 104 of the said injection device 100 (see FIG. 2). The first abutment member 40 may be arranged at a proximal or a distal end of the holder 4.

Preferably, the second abutment member 60 is parallel to the first abutment member 40. As represented on FIG. 3, the second abutment member 60 thus defines a distal abutment surface 62, said distal abutment surface 62 being configured to abut against a proximal face of the needle cover 102. This proximal face may be defined at a proximal end 114 of the needle cover 102. The respective proximal and distal abutment surfaces 42, 62 may extend orthogonally to the translational direction X. The second abutment member 60 may be preferably arranged at a proximal end of the needle cover remover 6.

With reference to FIG. 2, the first and the second abutment members 40, 60 are preferably shaped so as to insert into a groove 116 delimited between the barrel 104 and the needle cover 102 in the initial position. More specifically, the first and the second abutment members 40, 60 may insert between the distal shoulder of the barrel 104 and the proximal end 114 of the needle cover 102. To that end, the first and/or the second abutment member 40, 60 may be preferably plate-shaped, as shown on FIG. 3. The plate-shaped first and second abutment members 40, 60 are orthogonal to the translation direction X.

As illustrated on FIG. 3, one or both of the first and second abutment members 40, 60 delimits a notch 44, 64 configured to receive the distal tip 108 of the injection device 100, or the flange 106 of the injection device 100. Preferably, both the first and second abutment members 40, 60 delimits a notch 44, 64. The notches 44, 64 are opened at their top end, having regard to a vertical direction Z orthogonal to the top plate 22 and to the longitudinal direction X, so as to allow a user to put the injection device 100 down onto the holder 4 and the needle cover remover 6. The injection device 100, preferably the distal tip 108 of the injection device 100, thus extends through these notches 44, 64, which are aligned with regard to direction X. For example, the notches 44, 64 may be U-shaped.

In order to support the injection device 100, the holder 4 may comprise a longitudinal recess 46 configured to receive the barrel 104 of the injection device 100. The longitudinal recess 46 and the barrel 104 may be complementarily shaped. For instance, the longitudinal recess 46 has a cylindrical shape, more specifically a hemicylindrical shape. The longitudinal recess 46 indeed delimits a longitudinal top opening in order to allow a user to put the injection device 100 down inside this longitudinal recess 46.

The longitudinal recess 46 has a proximal end 460*b* and a distal end 460*a* opposite the proximal end 460*b*. The first abutment member 40 preferably extends at one of said proximal and distal ends of the longitudinal recess 46.

With reference to FIGS. 2 and 3, the holder 4 advantageously comprises a retaining element 48, that may be plated shaped, configured to block or limit a proximal translation of the injection device 100. The retaining element 48 is preferably fixed to the holder 4. The retaining element 48 may be a distal blocking surface 480 configured to block a proximal face of the flange 106 of the injection device 100. The distal blocking surface 480 faces the proximal end 460*b* of the longitudinal recess 46 and defines therebetween a hole 482 that is shaped to receive the flange 106 of the injection device 100. The distance between the distal blocking surface 480 and the proximal end 460*b* of the longitudinal recess 46 of the holder 4 is preferably greater than the flange 106 width of the injection device 100. The retaining element 48 may also comprise a notch 484, such as a U-shaped notch, for receiving the plunger rod 110 of the injection device 100. This notch 484 may be aligned with the notches 44, 64 and the longitudinal recess 46 regard to the longitudinal direction X.

Figure 7:
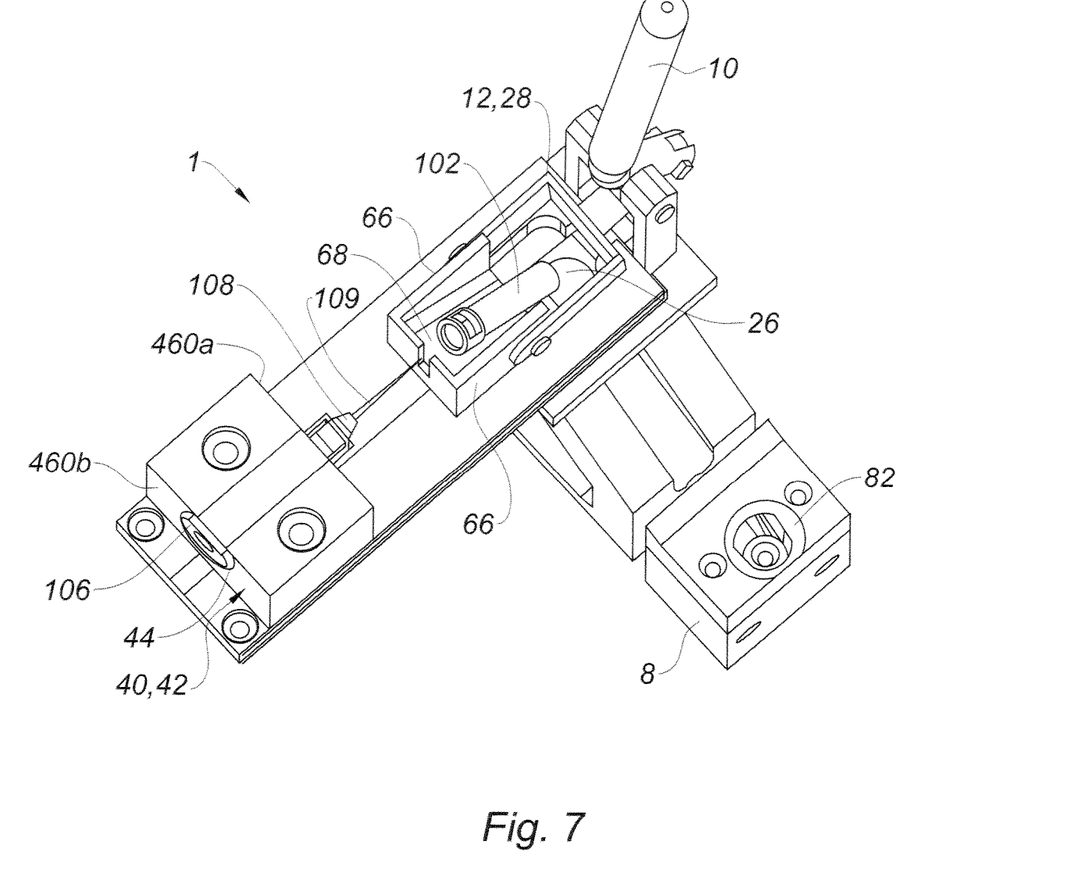
FIG. 7 is partial top view of a removing device according to an embodiment of the invention.

With reference for example to FIGS. 2 and 7, the needle cover remover 6 comprises two protective walls 66, for example plate-shaped protective walls 66, configured to extend on each sides of the needle cover 102 so as to guide the needle cover 102 during the ejection movement and then to protect a user from the uncovered needle. The two protective walls 66 may be parallel to each other and/or parallel to the direction X. As shown on FIG. 2 or FIG. 7, the protective walls 66 extend from the second abutment member 60, possibly until a distal end of the needle cover remover 6.

As visible on FIG. 7, the needle cover remover 6 may have a guiding ramp 68 configured to guide the removed needle cover 102 towards a collecting area. This guiding ramp 68 may extend from the second abutment member 60 and slope down towards the distal end of the needle cover remover 6. The guiding ramp 68 may extend between the two protective walls 66, and may thus form the bottom wall of a guiding portion of the needle cover remover 6 while the protective walls 66 form lateral walls of this guiding portion.

Advantageously, the collecting area is defined by a collector 8 that may be arranged inside the housing 2 (FIG. 2) or outside the housing 2 (FIG. 4). The collector 8 is configured to collect one or several needle covers 102 immediately after their removal.

With reference to FIG. 2, the collector 8 may comprise a drawer that may be removable from the housing 2 to allow a user to empty the collector 8, for example by spilling the removed needle covers 102 into a waste container. For instance, the collector 8 is movable relative to the housing in a transversal direction that is orthogonal the longitudinal and vertical directions X, Z.

With reference to FIG. 4, the collector 8 is fixed to the housing 2. The collector 8 may be configured to receive a single removed needle cover 102. Furthermore, the collector 8 may be configured to maintain the removed needle cover 102 in a predetermined position, for example in a upright position, such that a user may advantageously put the needle cover 102 back onto the injection device 100 without having to grasp this needle cover 102. To that end, the collector 8 may comprise a well 80 delimiting an access opening 82 at its top end. The well 80 extends in the vertical direction Z. The well 80 may have a bottom portion that is shaped complementarily to the needle cover 102. The proximal end 114 of this needle cover 102 is intended to be arranged close to the access opening 82. The distal end of the needle cover 102 stands on a bottom of the well 80.

The housing 2 comprises a through-hole 26, that may be arranged through the top plate 22 of the housing 2. This through-hole 26 allows the removed needle covers 102 to drop from the needle cover remover 6, that is positioned above this top plate 22, to the collector 8, that is positioned beneath the top plate 22. The through-hole 26 thus gives access to the collector 8. In the ejection position, the distal end of the needle cover remover 6 is located next to or above the through-hole 26 so that the removed needle cover 102 may fall down into the collecting area due to gravity, as illustrated on FIG. 7.

In order to allow a reliable drop of the removed needle covers 102 into the collecting area, the removing device 1 may advantageously comprise guiding means configured to guide the removed needle cover 102 into the collector 8.

The guiding means may comprise an introducer 28 configured to guide the removed needle cover 102 towards the through-hole 26. The introducer 28 also prevents the removed needle cover 102 from being projected outside the removing device 1. In the ejection position, the needle cover remover 6 is configured to be located at one side of the through-hole 26 while the introducer 28 is configured to be located at an opposite side of this through-hole 26. The introducer 28 may include a concave, curved, or plate-shaped wall onto which the ejected needle cover 102 may rebound before dropping through the hole.

As shown on FIG. 2, the introducer 28 may be a shell extending above the through-hole 26 and defining an aperture facing the needle cover remover 6 so as to receive the removed needle cover 102. As shown on FIG. 5, the introducer 28 may be a portion of a connecting rod 12 that forms part of the displacement means.

Figure 6:
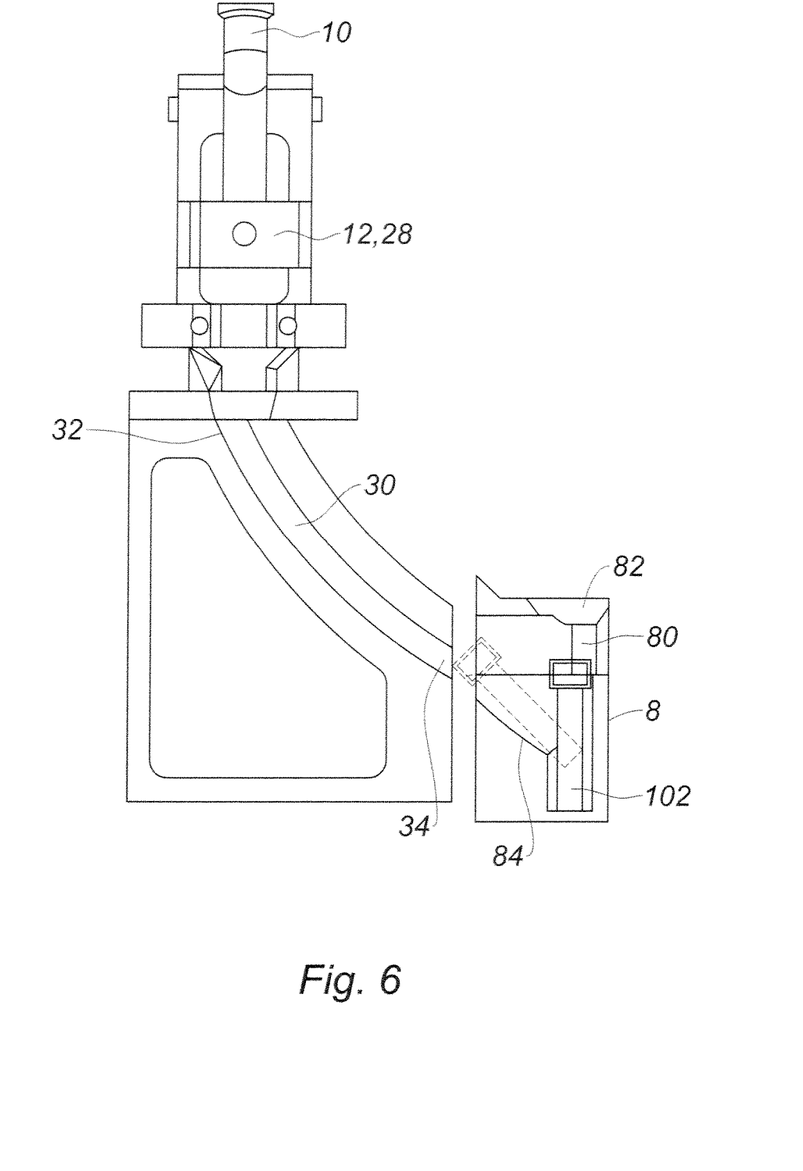
FIG. 6 is a partial cross-section of a removing device according to an embodiment of the invention.

With reference to FIG. 6, the guiding means may also comprise a guiding channel 30 extending from the through-hole 26 to the collector 8 to guide by gravity the removed needle cover 102 into the collector 8. The guiding channel 30 has an entry opening 32 arranged below the through-hole 26 and an exit opening 34 leading into a lateral side of the collector 8. The collector 8 may have a ramp portion 84 extending the guiding channel 30 until the well 80.

It should be noted that the collector 8, the housing 2, and/or the guiding means, such as the introducer 28, may include at least one transparent wall or window allowing a user to see if the collector 8 is full or empty.

With reference to FIG. 2, the displacement means advantageously comprise an actuator 11, which may be electric, such as an electric motor or a mechanical actuator, configured to move the needle cover remover 6 relative to the holder 4, from the initial position to the ejection position, and/or from the ejection position to the initial position. The displacement means are preferably arranged inside the housing 2. The removing device 1 may further include energy storage means, such as a battery, configured to feed the actuator during use of the removing device 1. The energy storage means may be also arranged inside the housing 2. In embodiments, the removing device 1 comprises a sensor 36, such as a microswitch as shown on FIG. 3, configured to detect that an injection device 100 is supported by the holder 4. If no injection device 100 is detected, the removing device 1 may be configured to prevent the user from activating the displacement means. The sensor may be arranged in the holder 4, more specifically in the longitudinal recess 46, as shown on FIG. 3. The removing device 1 may comprise a push button (not shown) allowing a user to activate the displacement means.

With reference to FIGS. 4 to 7, the displacement means may alternatively be manuel displacement means. The displacement means may comprise a handle 10 rotatably mounted onto the housing 2 relative to the transversal direction Y, between a rest position, which may correspond to the initial position of the needle cover remover 6, and an activation position, which may correspond to the ejection position of the needle cover remover 6. The displacement means further comprise a connecting rod 12 coupling the handle 10 to the needle cover remover 6, or possibly the holder 4 if the holder 4 is movable relative to the housing 2. The rotation of the handle 10 from the rest position to the activation position causes the needle cover remover 6 and the holder 4 to move away from each other in order to pull the needle cover 102 off. The handle 10 may be configured to go back to its rest position by gravity, or by a force exerted by the user. It should be noted that the connecting rod 12 may be connected to the needle cover remover 6 by two arms that are connected to each other by an intermediate portion which may form the introducer 28.

Although not shown on the figures, the displacement means may comprise a spring configured to move one or both of the needle cover remover 6 and the holder 4 relative to each other, for example back to the initial position after the removal of the needle cover 102.

With reference to FIG. 2, the device 1 comprises a preparatory support 29 configured to support a second injection device 100, meanwhile removing the needle cover 102 of a first injection device 100 that is being supported by the holder 4. The preparatory support 29 may be affixed onto the top plate 22 of the housing 2. The preparatory support 29 is preferably adjacent to the holder 4. The preparatory support 29 comprises a longitudinal recess 290 which may be similar to the longitudinal recess 46 of the holder 4, for example a partially cylindrical or hemicylindrical recess. The longitudinal recess 290 is configured to receive the barrel 104 of said second injection device 100. The longitudinal recess 290 of the preparatory support 29 may extend parallel to the longitudinal recess 46 of the holder 4.

The invention also relates to a method for removing the needle cover 102 of an injection device 100 by means of the above described removing device 1. The method comprises the steps of:
  positioning a first injection device 100 on the holder 4 of the removing device 1, so that the first abutment member 40 abuts against said injection device 100, preferably against the barrel 104 or the flange 106 of said injection device 100, more preferably against a distal face of the barrel 104 or of the flange 106 of said injection device 100, and the second abutment member 60 abuts or faces the needle cover 102, preferably abuts against a proximal face of the needle cover 102, and
  activating the displacement means so that the first and second abutment members 40, 60 move away from each other, thereby pulling needle cover 102 off the first injection device 100.

Advantageously, during the step of activating the displacement means of the method of the invention, the second abutment member 60 translationally moves away from the first abutment member 40.

The method may further comprise one or several of the steps listed below:
  positioning a second injection device 100 on the preparatory support 29;
  removing the first injection device 100 from the holder 4;
  after removal of a first injection device 100 from the holder 4, positioning a second injection on this holder 4 and repeat the same steps as for the first injection device 100;
  removing the collector 8 from the housing 2 in order to spill any removed needle cover 102 in a waste container, and placing the collector 8 back into the housing 2.

The invention claimed is:

1. A removing device configured to remove a needle cover removably mounted on a distal tip of an injection device comprising a barrel, the removing device comprising:
  a housing including a holder configured to hold the injection device and a needle cover remover configured to remove the needle cover from the injection device;
  a first abutment member provided on the holder, and being configured to abut against said injection device;
  a second abutment member provided on the needle cover remover, and being configured to abut against the needle cover; and
  displacement means configured to displace the needle cover remover relative to the holder in a translational direction so that the first and second abutment members translationally move away from each other in order to separate the needle cover from the injection device,
  wherein the first and second abutment members have a notch configured to receive a portion of the injection device, said notches being opened at their top end with regard to a vertical direction orthogonal to the translational direction to allow a user to put the injection device down onto the holder and the needle cover remover, wherein the first abutment member is configured to abut against a distal shoulder of the barrel of said injection device, the first and second abutment members contacting each other in an initial position of the needle cover remover relative to the holder.

2. The removing device according to claim 1, wherein the first abutment member is configured to abut against a distal face of a proximal flange of the barrel of said injection device.

3. The removing device according to claim 2, wherein the displacement means comprise a handle graspable by a user and rotatably mounted onto the housing between a rest position and an activation position, and a connecting rod coupling the handle to the second abutment member so that rotation of the handle from the rest position to the activation position causes the second abutment member and the first abutment member to move away from each other in order to pull off the needle cover.

4. The removing device according to claim 1, wherein the displacement means comprise an actuator.

5. The removing device according to claim 4, wherein the actuator is electric.

6. The removing device according to claim 1, wherein one or both of the first and second abutment members are configured to insert into a groove delimited between the barrel and the needle cover.

7. The removing device according to claim 1, wherein at least one of the first and second abutment members is plate-shaped.

8. The removing device according to claim 1, wherein the holder comprises a longitudinal recess configured to support the barrel of the injection device, said longitudinal recess having a proximal end and a distal end opposite the proximal end, the first abutment member extending either at the proximal or at the distal end of said longitudinal recess.

9. The removing device according to claim 1, wherein the housing comprises a retaining element configured to block a proximal movement of a flange of the injection device.

10. The removing device according to claim 1, wherein the needle cover remover comprises at least one wall configured to extend on at least one side of the needle cover.

11. The removing device according to claim 1, wherein the removing device comprises a sensor configured to detect that the injection device is supported by the holder.

12. The removing device according to claim 1, wherein the housing comprises a preparatory support configured to support another injection device next to the holder.

13. A method for removing a needle cover of an injection device, said method comprising the steps of:
 positioning the injection device on a holder of the removing device according to claim 1, so that the first abutment member abuts against the injection device, and the second abutment member abuts against the needle cover; and
 activating the displacement means so that the first and second abutment members move away from each other, thereby pulling the needle cover off the injection device.

\* \* \* \* \*